US011022619B2

(12) United States Patent
Macintyre et al.

(10) Patent No.: US 11,022,619 B2
(45) Date of Patent: *Jun. 1, 2021

(54) DEVICES, SYSTEMS, AND METHODS FOR MEASURING BLOOD LOSS

(71) Applicant: University of Utah Research Foundation, Salt Lake City, UT (US)

(72) Inventors: Annette Macintyre, Salt Lake City, UT (US); Lara Brewer, Bountiful, UT (US); Suzanne Wendelken, Salt Lake City, UT (US); Quinn Tate, North Salt Lake, UT (US); Soeren Hoehne, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 257 days.

This patent is subject to a terminal disclaimer.

(21) Appl. No.: 16/055,745

(22) Filed: Aug. 6, 2018

(65) Prior Publication Data

US 2018/0372757 A1    Dec. 27, 2018

Related U.S. Application Data

(63) Continuation of application No. 14/890,098, filed as application No. PCT/US2014/037448 on May 9, 2014, now Pat. No. 10,041,960.

(Continued)

(51) Int. Cl.
*G01N 33/72* (2006.01)
*G01N 21/31* (2006.01)
(Continued)

(52) U.S. Cl.
CPC ....... *G01N 33/721* (2013.01); *A61B 5/02042* (2013.01); *A61B 5/1455* (2013.01);
(Continued)

(58) Field of Classification Search
CPC ......... G01N 33/72; G01N 21/31; G01N 33/49
(Continued)

(56) References Cited

U.S. PATENT DOCUMENTS 2,386,878 A    10/1945  Nickerson
3,068,742 A    12/1962  Hicks, Jr. et al.
(Continued)

FOREIGN PATENT DOCUMENTS

| JP | 56-35038 | * 4/1981 |
| WO | WO0117421 | 3/2001 |
| WO | WO2013173356 | 11/2013 |

OTHER PUBLICATIONS

Mainland, J.F., British Journal of Anaesthesia 1966, 38, 76-78.
(Continued)

*Primary Examiner* — Arlen Soderquist
(74) *Attorney, Agent, or Firm* — Morriss O'Bryant Compagni Cannon, PLLC

(57) ABSTRACT

Devices, systems, and methods for measuring the blood loss of a subject during a medical procedure. Blood and other fluids are received within a container, and a blood measurement device determines the hemoglobin concentration of the fluid within the container. The blood measurement device can also calculate the estimated blood loss of the subject based upon the determined hemoglobin concentration and the volume of the fluid within the container and the patient's hemoglobin.

16 Claims, 8 Drawing Sheets

Related U.S. Application Data

(60) Provisional application No. 61/821,937, filed on May 10, 2013.

(51) Int. Cl.
    *G01N 33/49*     (2006.01)
    *A61M 1/00*     (2006.01)
    *A61B 5/02*     (2006.01)
    *A61B 5/145*     (2006.01)
    *A61B 5/1455*     (2006.01)

(52) U.S. Cl.
    CPC ......... *A61B 5/14546* (2013.01); *A61M 1/006* (2014.02); *G01N 21/31* (2013.01); *G01N 33/49* (2013.01); *G01N 2333/805* (2013.01)

(58) Field of Classification Search
    USPC ....... 356/40; 422/82.05–82.07, 82.09, 82.11; 436/66, 164–165
    See application file for complete search history.

(56) References Cited

U.S. PATENT DOCUMENTS

| | | | | |
|---|---|---|---|---|
| 3,120,125 | A * | 2/1964 | Vasel | G01F 23/2927 73/293 |
| 3,123,066 | A * | 3/1964 | Brumley | A61B 5/1459 600/341 |
| 3,240,110 | A * | 3/1966 | Ohlin | A61B 5/02042 356/39 |
| 3,296,922 | A | 1/1967 | Goldberg | |
| 3,692,410 | A * | 9/1972 | Jurany | G01N 21/8507 356/40 |
| 3,794,428 | A * | 2/1974 | Giesecke | G01F 23/2921 356/434 |
| 3,995,168 | A | 11/1976 | Neuscheler et al. | |
| 4,119,860 | A * | 10/1978 | Gooley | G01F 23/2921 250/577 |
| 4,275,726 | A * | 6/1981 | Schael | A61M 1/02 210/929 |
| 4,305,659 | A | 12/1981 | Bilstad et al. | |
| 4,562,842 | A | 1/1986 | Morfeld et al. | |
| 4,680,475 | A * | 7/1987 | Tansony | G01F 23/292 250/577 |
| 4,745,929 | A * | 5/1988 | Silver | A61F 5/4405 250/577 |
| 4,773,423 | A | 9/1988 | Hakky | |
| 4,803,992 | A * | 2/1989 | Lemelson | A61B 1/00096 600/342 |
| 4,810,090 | A | 3/1989 | Boucher et al. | |
| 4,904,878 | A | 2/1990 | Gipp et al. | |
| 4,954,724 | A | 9/1990 | Koda et al. | |
| 5,029,584 | A | 7/1991 | Smith | |
| 5,031,642 | A * | 7/1991 | Nosek | A61B 5/02042 177/1 |
| 5,048,524 | A | 9/1991 | Bailey | |
| 5,231,032 | A | 7/1993 | Ludvigsen | |
| 5,235,179 | A * | 8/1993 | Chang | G01F 23/292 250/227.21 |
| 5,236,664 | A | 8/1993 | Ludvigsen | |
| 5,378,227 | A * | 1/1995 | O'Riordan | A61M 1/3624 604/19 |
| 5,478,479 | A * | 12/1995 | Herrig | A61M 1/02 210/745 |
| 5,709,670 | A | 1/1998 | Vancaillie et al. | |
| 5,734,464 | A | 3/1998 | Gibbs | |
| 5,747,824 | A * | 5/1998 | Jung | A61M 1/3624 250/577 |
| 5,756,940 | A | 5/1998 | Van Driel | A61M 1/3624 177/245 |
| 5,773,301 | A | 6/1998 | Ziegler | |
| 5,944,668 | A | 8/1999 | Vancaillie et al. | |
| 5,980,465 | A * | 11/1999 | Elgas | A61B 5/02755 128/898 |
| 6,063,051 | A * | 5/2000 | Stern | A61B 5/4283 600/579 |
| 6,064,474 | A | 5/2000 | Lee et al. | |
| 6,291,824 | B1 | 9/2001 | Battarbee et al. | |
| 6,543,493 | B2 * | 4/2003 | Jursich | G01F 23/2927 137/93 |
| 6,718,190 | B2 | 4/2004 | Krivitski et al. | |
| 6,831,733 | B2 | 12/2004 | Pettersson et al. | |
| 7,119,689 | B2 | 10/2006 | Mallett et al. | |
| 7,710,567 | B1 | 5/2010 | Mentzer et al. | |
| 7,768,646 | B1 * | 8/2010 | Mentzer | G01N 21/431 356/436 |
| 7,981,073 | B2 | 7/2011 | Mollstam et al. | |
| 8,072,594 | B1 | 12/2011 | McMahon | |
| 8,157,775 | B2 * | 4/2012 | Bobroff | A61M 1/0003 604/319 |
| 8,219,170 | B2 | 7/2012 | Hausmann et al. | |
| 8,493,441 | B2 | 7/2013 | Thonhauser | |
| 10,041,960 | B2 * | 8/2018 | MacIntyre | A61M 1/006 |
| 10,285,596 | B2 * | 5/2019 | Akerman | A61B 5/02042 |
| 10,690,684 | B2 * | 6/2020 | Macintyre | G01N 21/31 |
| 2001/0004285 | A1 * | 6/2001 | Cadell | G01N 21/3103 356/39 |
| 2002/0058342 | A1 | 5/2002 | Lilja et al. | |
| 2003/0010396 | A1 * | 1/2003 | Jursich | G01F 23/2927 141/94 |
| 2003/0123047 | A1 | 7/2003 | Pettersson et al. | |
| 2005/0065820 | A1 | 3/2005 | Mallett et al. | |
| 2005/0203469 | A1 * | 9/2005 | Bobroff | A61M 1/0023 604/318 |
| 2005/0209585 | A1 | 9/2005 | Nord et al. | |
| 2005/0243303 | A1 | 11/2005 | Pettersson et al. | |
| 2006/0013725 | A1 | 1/2006 | Larsen | |
| 2006/0177347 | A1 | 8/2006 | Larsen et al. | |
| 2006/0280216 | A1 | 12/2006 | Jayaraman | |
| 2007/0060809 | A1 | 3/2007 | Higgins | |
| 2007/0135779 | A1 | 6/2007 | Lalomia et al. | |
| 2008/0000485 | A1 * | 1/2008 | Williams | A61B 50/10 128/897 |
| 2008/0071154 | A1 | 3/2008 | Hausmann et al. | |
| 2008/0114301 | A1 * | 5/2008 | Bandhauer | A61M 1/0023 604/153 |
| 2008/0179344 | A1 | 7/2008 | Michaels et al. | |
| 2008/0243054 | A1 * | 10/2008 | Mollstam | A61M 3/0216 604/31 |
| 2009/0013780 | A1 * | 1/2009 | Gao | A61M 1/0023 73/293 |
| 2009/0043212 | A1 * | 2/2009 | Ranucci | G16H 40/63 600/484 |
| 2009/0054908 | A1 | 2/2009 | Zand et al. | |
| 2009/0075324 | A1 | 3/2009 | Pettersson | |
| 2009/0187131 | A1 | 7/2009 | Fitzgerald et al. | |
| 2009/0240119 | A1 | 9/2009 | Schwaibold et al. | |
| 2010/0003714 | A1 * | 1/2010 | Bachur, Jr. | G01N 33/4925 435/29 |
| 2010/0110416 | A1 * | 5/2010 | Barrett | A61B 5/14535 356/40 |
| 2010/0134303 | A1 | 6/2010 | Perkins | |
| 2010/0160754 | A1 | 6/2010 | Durkin et al. | |
| 2010/0249550 | A1 | 9/2010 | Lovejoy | |
| 2010/0298658 | A1 | 11/2010 | McCombie et al. | |
| 2011/0063433 | A1 | 3/2011 | Thonhauser | |
| 2011/0112435 | A1 | 5/2011 | Ramanujam et al. | |
| 2011/0112472 | A1 * | 5/2011 | Jacobson | A61M 5/16804 604/67 |
| 2012/0035417 | A1 | 2/2012 | Mollstam et al. | |
| 2012/0078137 | A1 * | 3/2012 | Mendels | G01F 23/2921 600/584 |
| 2013/0006116 | A1 | 1/2013 | Kim et al. | |
| 2013/0011042 | A1 * | 1/2013 | Satish | G06T 5/00 382/134 |
| 2013/0301901 | A1 | 11/2013 | Satish et al. | |
| 2013/0303870 | A1 | 11/2013 | Satish et al. | |
| 2013/0324815 | A1 * | 12/2013 | Jian | G01N 21/474 600/327 |

(56) References Cited

U.S. PATENT DOCUMENTS

| | | |
|---|---|---|
| 2013/0338458 A1 | 12/2013 | Bechtel et al. |
| 2014/0128838 A1 | 5/2014 | Satish et al. |
| 2015/0168371 A1* | 6/2015 | Babson .................. G01N 33/49 356/40 |

OTHER PUBLICATIONS

Brant, H. A. et al, Journal of Obstetrics and Gynaecology of the British Commonwealth 1966, 73, 456-459.

Paton, J.S. et al., Lancet 1977, 310, 744-745.

Lewis, S.M. et al., Lauryl sulphate haemoglobin; a non-hazardous substitute for HiCN in haemoglobinometry. Clin Lab Haematol. 1991; 13(3):279-90.

Oshiro, I. et al., New method for hemoglobin determination by using sodium lauryl sulfate (SLS). Clin Biochem. 1982: 15(2):83-8.

Vanzetti, G., An azide-methemoglobin method for hemoglobin determination In blod. J Lab Clin Med. 1966; 67(1):116-26.

Zijlstra, W.G. et al., Standardization of hemoglobinometry. I. The extinction coefficient of hemiglobincyanide. Clin Chim Acta. 1960; 5:719-26.

International Search Report and Written Opinion dated Sep. 26, 2014 for Application No. PCT/US2014/037448, which was filed on May 9, 2014 and published as WO 2014/183003 dated Nov. 13, 2014 (Applicant-University of Utah Research Foundation) (11 pages).

International Prliminary Report on Patentability dated Nov. 10, 2015 for Application No. PCT/US2014/037448, which was filed on May 9, 2014 and published as WO 2014/183003 dated Nov. 13, 2014 (Applicant—University of Utah Research Foundation) (9 pages).

European Search report and Written Opinion dated Dec. 1, 2016 by the International Searching Authority for EP Application No. 14794433.4 dated May 9, 2014 and published as 2994042 dated Mar. 16, 2016 (Applicant—University of Utah Research Foundation) (6 pages).

von Schenck, H. et al., Clinical Chemistry 1986, 32, 526-529.

* cited by examiner

DEVICES, SYSTEMS, AND METHODS FOR MEASURING BLOOD LOSS

CROSS-REFERENCE TO RELATED APPLICATIONS

This application is a continuation of U.S. patent application Ser. No. 14/890,098, filed Nov. 9, 2015, which is a national phase entry under 35 U.S.C. § 371 of International Application No. PCT/US2014/037448, filed May 9, 2014, which claims the benefit of the filing date of U.S. Provisional Patent Application No. 61/821,937, filed May 10, 2013, the entirety of each of which is hereby incorporated by reference.

FIELD

This invention relates to devices, systems, and methods for measuring the blood loss of a subject, and more particularly, to devices, systems, and methods for measuring the blood loss of a subject during a medical procedure.

BACKGROUND

During a surgical procedure, it is necessary to assess the amount of patient blood loss in order to determine whether a transfusion of blood or other intravenous (IV) fluid is needed. Unnecessary blood transfusions, coupled with over/under administration of IV fluids, are frequently associated with poor patient outcomes. Conventionally, during a medical procedure, a suction canister collects blood, irrigation fluids and other bodily fluids. The current methods for estimating intraoperative blood loss are inaccurate due to the difficulty of determining the amount of blood in the suction canister when the blood is mixed with unknown quantities of other fluids within the suction canister.

Thus, there is a need in the pertinent art for devices, systems, and methods for accurately and quickly measuring the blood loss of a subject during a surgical procedure.

SUMMARY

Described herein, in one aspect, is a blood measurement device for determining the amount of blood of a subject within a fluid sample. The blood measurement device includes a light source, at least one photodetector, and a processor. The light source is configured to selectively generate light at a first wavelength and at a second wavelength different from the first wavelength. The light source and the at least one photodetector are configured for positioning in an operative position. In the operative position, the at least one photodetector is configured to receive at least a portion of the light generated by the light source. Upon positioning of the light source and the at least one photodetector in the operative position, the at least one photodetector is configured to produce a first signal indicative of the absorbance of the fluid sample at the first wavelength and a second signal indicative of the absorbance of the fluid sample at the second wavelength. The processor is operatively coupled to the at least one photodetector and is configured to receive the first and second signals from the at least one photodetector. Based upon the received first and second signals, the processor can be configured to determine the concentration of hemoglobin within the fluid sample. Optionally, the processor can be further configured to determine the volume of blood within the fluid sample. Also described is a blood measurement system including the blood loss measurement device and a processor. Each photodetector of the blood loss measurement device can be configured to produce a first signal indicative of the absorbance of the fluid sample at the first wavelength and a second signal indicative of the absorbance of the fluid sample at the second wavelength. The processor can be in operative communication with the at least one photodetector, and the processor can be configured to receive the first and second signals from each photodetector. The processor can be configured to determine the concentration of hemoglobin within the fluid sample. The processor can be further configured to determine the volume of the fluid sample. The processor can be still further configured to determine the blood loss of the subject.

Also disclosed are blood measurement systems including the blood measurement device and a container, such as a suction canister. Optionally, portions of the blood measurement device can be selectively insertable within a fluid sample positioned within the suction canister.

Methods of determining the blood loss of a subject are also disclosed. The methods can include operatively positioning the blood measurement device relative to a fluid sample and using the blood measurement device (alone or in combination with conventional methods) to determine the concentration of hemoglobin within the fluid sample. Optionally, the methods can include administering one or more reagents to the interior space of the suction canister. Optionally, the reagents can be configured to convert hemoglobin within the fluid sample into either methemoglobin or sulphemoglobin. The methods can optionally include the step of delivering an anti-coagulant to the fluid sample.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

Figure 3:
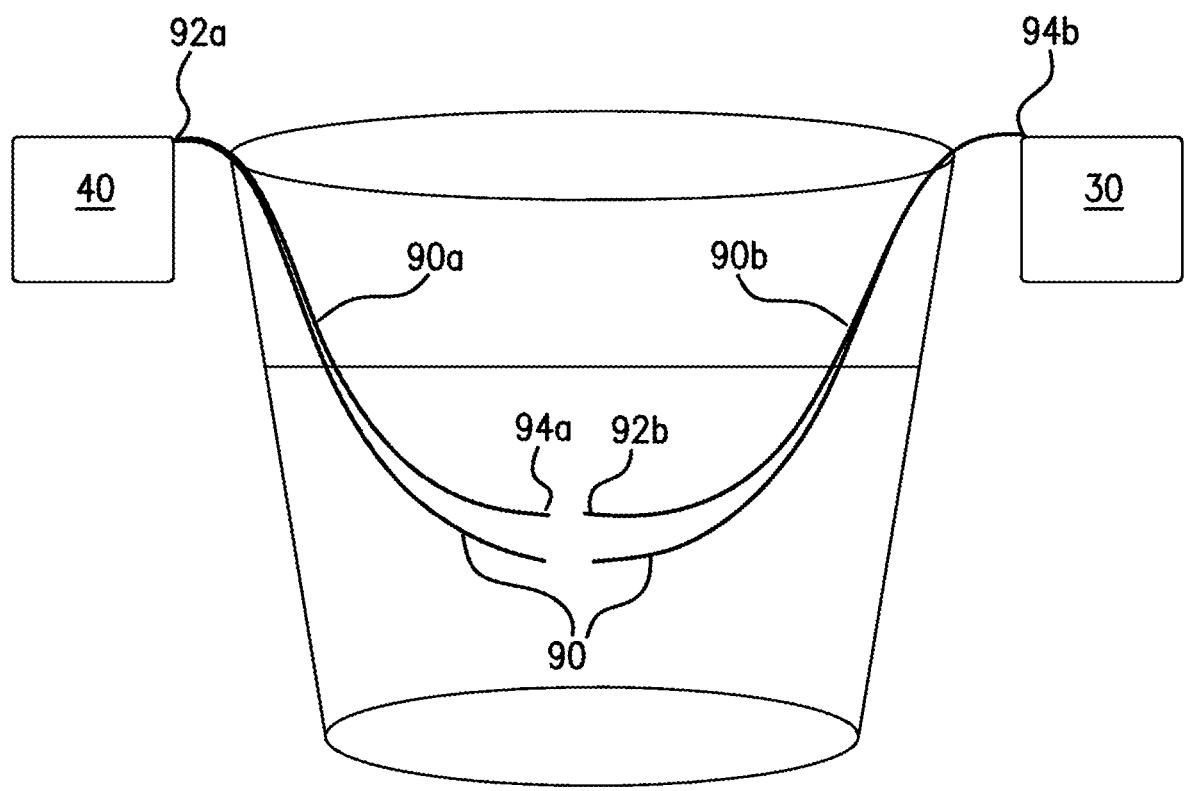

FIG. 3 schematically depicts another exemplary blood measurement system as disclosed herein, showing a single pair of optical fibers positioned within a sample fluid as disclosed herein.

Figure 4:
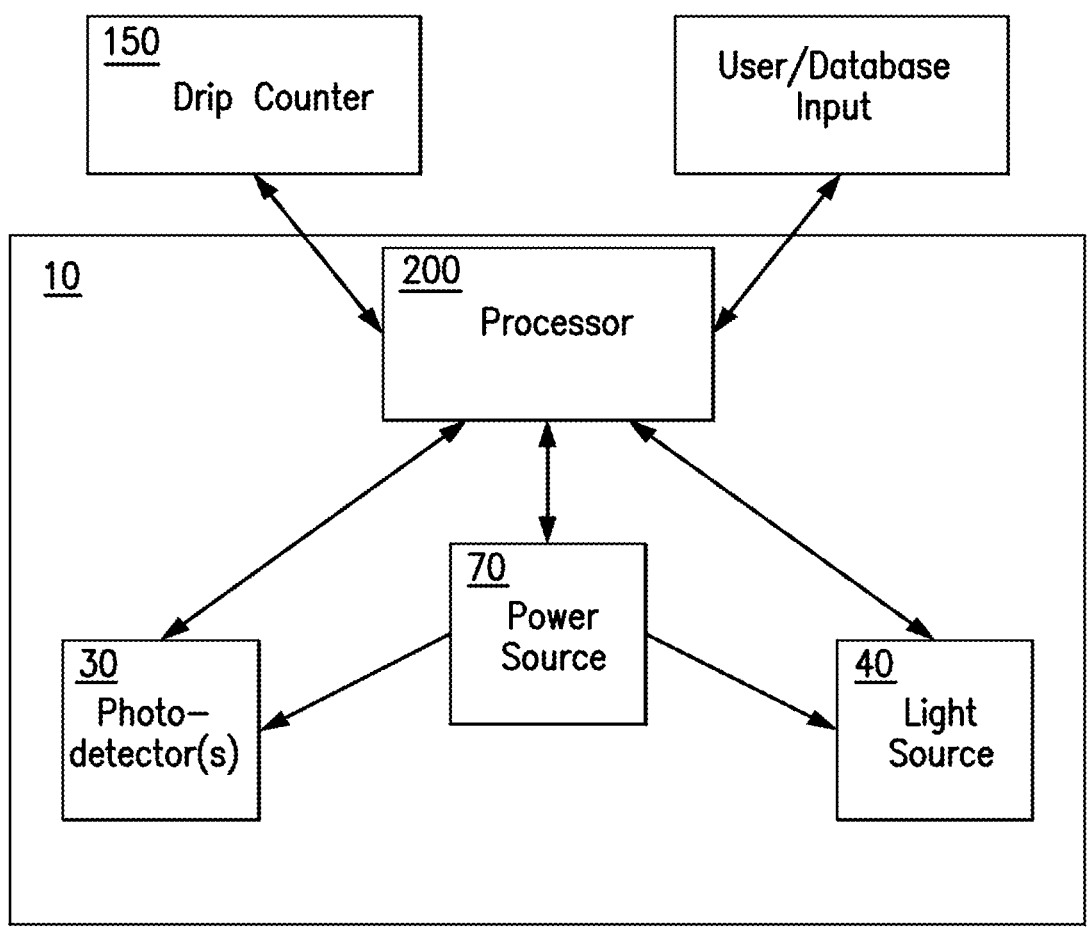

FIG. 4 schematically depicts an exemplary blood measurement system as disclosed herein.

Figure 5:
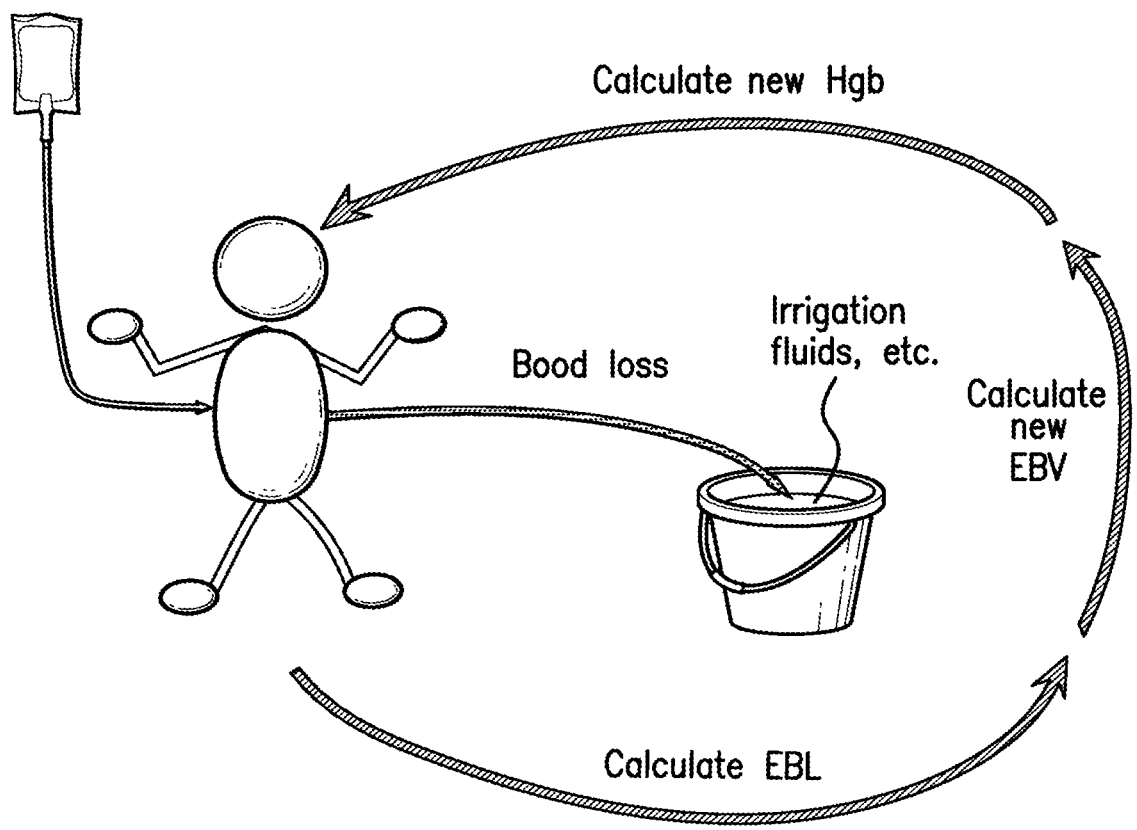

FIG. 5 depicts an exemplary process of calculating the updated hemoglobin levels and blood loss for a subject during a surgical procedure. EBL refers to "estimated blood loss," EBV refers to "estimated subject blood volume," and Hgb refers to the hemoglobin concentration of the subject.

Figure 6:
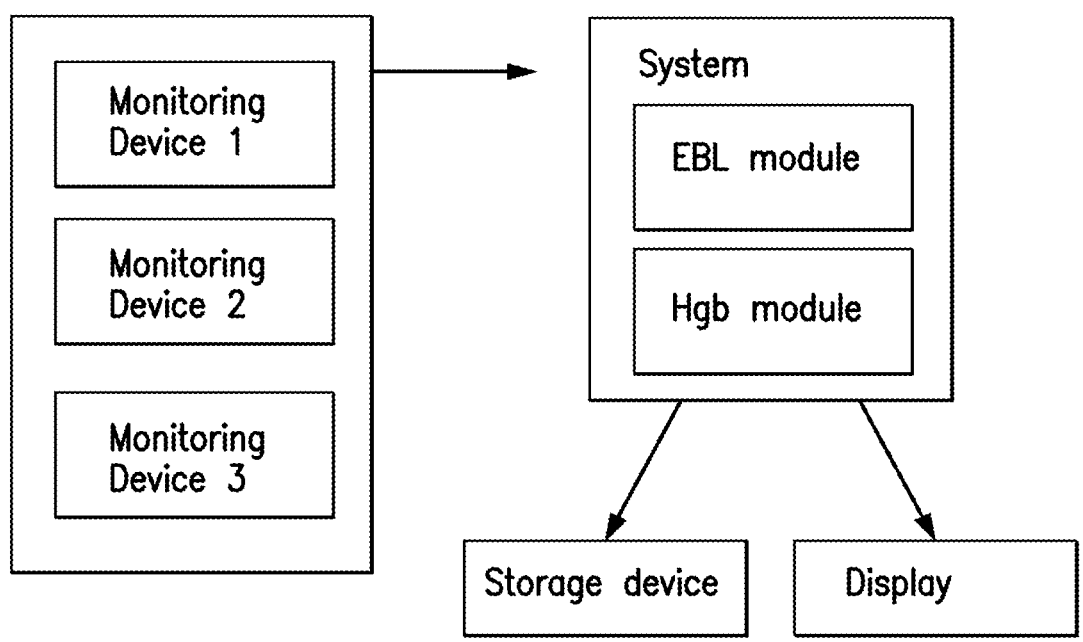

FIG. 6 depicts an exemplary relationship among the monitoring devices, system, storage and display disclosed herein.

Figure 7:
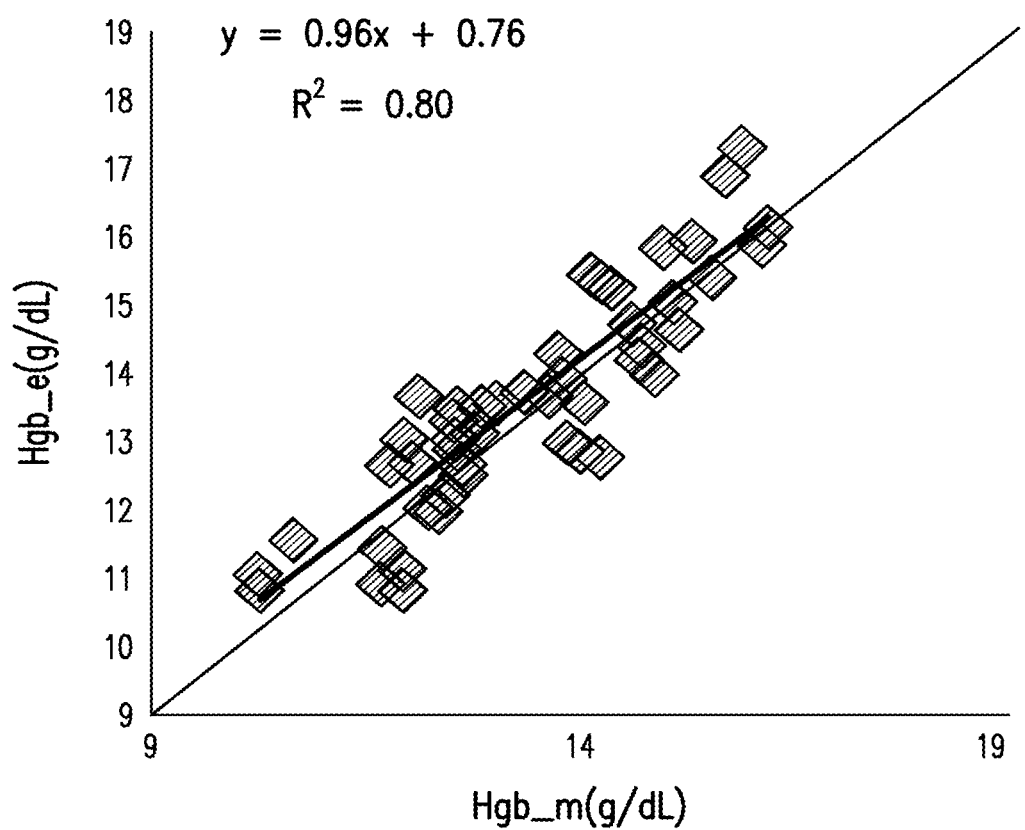

FIG. 7 depicts a linear regression analysis of predicted hemoglobin concentration and measured hemoglobin concentration using an exemplary system as disclosed herein. $R^2$ was calculated as 0.80.

Figure 8:
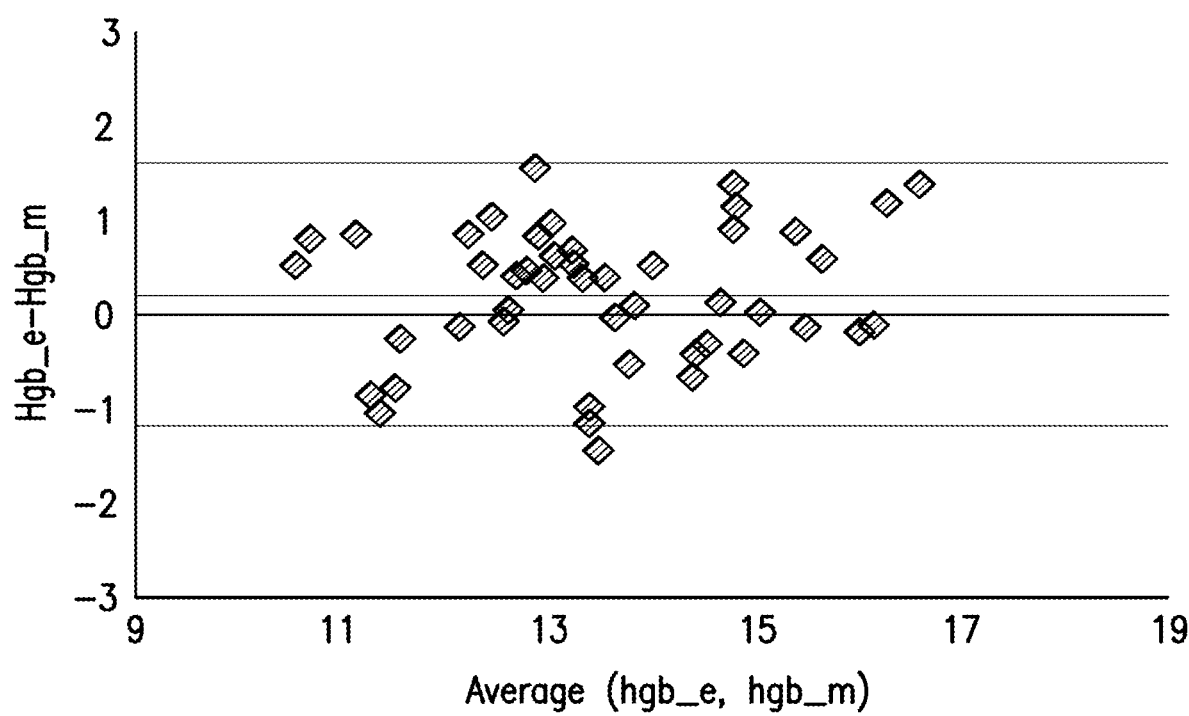

FIG. 8 depicts a Bland-Altman analysis of predicted patient hemoglobin and measured patient hemoglobin using an exemplary system as disclosed herein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a photodetector" can include two or more such photodetectors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

Described herein with reference to FIGS. 1-6 are devices, systems, and methods for measuring blood loss within a subject. It is contemplated that the disclosed devices, systems, and methods can provide a more accurate measurement of blood loss during a surgical procedure than conventional devices, systems, and methods. As further disclosed herein, the disclosed systems and methods can be used to iteratively estimate the hemodilution of a subject based on the kinetics of intravenous fluid administration and blood loss. It is further contemplated that the disclosed blood measurement devices and systems can directly measure the amount of blood in a suction canister based upon the estimated hemodilution of the subject. Thus, it is contemplated that the disclosed system can iteratively estimate the hemoglobin status of the subject intraoperatively by taking into account a baseline estimation of the patient's intravascular blood volume (EBV) and preoperative hemoglobin status, the volume of intravenous fluids administered to the subject, as well as the volume and hemoglobin concentration of the fluid within the suction canister. The updated estimated hemoglobin status of the subject can then be used to accurately calculate the new volume of blood loss in the suction canister.

As further described herein, it is contemplated that the disclosed devices, systems, and methods can optionally employ algorithms to determine the concentration of hemoglobin within a fluid sample and/or the blood loss experienced by a subject during a medical procedure. However, it is contemplated that the disclosed devices, systems, and methods can be used in conjunction with any conventional method of predicting a subject's hemoglobin concentration and/or the volume of a fluid sample containing the blood of a subject. Thus, although exemplary algorithms for determining hemoglobin concentration and blood loss are provided herein, it is understood that the devices, systems, and methods disclosed herein are not restricted to use with particular algorithms. For example, when the hemoglobin concentration within a fluid sample and the volume of the fluid sample are known (i.e., provided as an input to the processor of the device or determined by the device), it is contemplated that the disclosed devices, systems, and methods can be used in conjunction with conventional methods for determining one or more of the following: the subject's preoperative hemoglobin concentration; an updated hemoglobin concentration of the subject, determined from a subject's blood sample; an updated hemoglobin concentration of the subject, based upon an estimate provided by a practitioner (e.g., an anesthesiologist); or an updated hemoglobin concentration of the subject, based upon a continuous, non-invasive method as is known in the art. It is contemplated that, when an updated hemoglobin concentration of the subject is determined, the preoperative hemoglobin concentration of the subject can be averaged with the updated hemoglobin concentration to permit determination of the amount of blood lost by the subject. It is further contemplated that the averaged hemoglobin concentration can be provided to a processor as disclosed herein in the form of one or more user inputs.

Blood Measurement Device

In one aspect, and with reference to FIGS. 1-4, a blood measurement device 10 can comprise means for measuring the concentration of hemoglobin within the fluid sample 12.

In exemplary aspects, at least a portion of the fluid sample can comprise blood of a subject.

In another aspect, as shown in FIGS. 1-4, the means for measuring the concentration of hemoglobin can comprise at least one photodetector 30. In these aspects, it is contemplated that the at least one photodetector 30 can comprise at least one photometer as is known in the art.

In additional aspects, the means for measuring the concentration of hemoglobin can further comprise a light source 40. In these aspects, the light source 40 can be configured to generate light at a first wavelength and at a second wavelength different from the first wavelength. It is contemplated that the light source 40 can comprise any conventional light source that is capable of generating light at multiple wavelengths.

In exemplary aspects, the light source 40 and the at least one photodetector 30 can be configured for positioning in an operative position. In the operative position, the at least one photodetector 30 can be configured to receive at least a portion of the light generated by the light source 40. It is contemplated that the at least one photodetector 30 can be configured to detect the absorbance of the fluid sample 12 at the first wavelength and the second wavelength. In exemplary aspects, the first wavelength can range from about 500 nm to about 600 nm and the second wavelength can range from about 850 nm to about 900 nm. Optionally, it is contemplated that the first wavelength can be about 525 nm and the second wavelength can be about 870 nm. Upon positioning of the light source 40 and the at least one photodetector 30 in the operative position, the at least one photodetector 30 can be configured to produce a first signal indicative of the absorbance of the fluid sample 12 at the first wavelength and a second signal indicative of the absorbance of the fluid sample at the second wavelength.

In exemplary aspects, the blood measurement device 10 can further comprise a processor 200 as is conventionally known in the art. In exemplary aspects, the processor 200 can be provided in the form of a computer, and the processor 200 can be in operative communication with a memory (or other storage device) and/or a display as are known in the art. It is contemplated that the memory can optionally store software that, when executed, is configured to perform one or more of the steps and calculations disclosed herein. It is further contemplated that the memory can store historical information related to the hemoglobin concentration and/or blood loss of particular patients. In exemplary optional aspects, the processor 200 can be provided as a microcontroller that is secured to or housed within a portion of the device 10. As further disclosed herein, the processor 200 can comprise one or more modules for determining at least one of the estimated blood loss (EBL) of the subject, the hemoglobin concentration (Hgb) of the fluid sample, and the volume of the fluid sample. In exemplary aspects, the processor 200 can be configured to receive one or more inputs from a user or a memory indicative of at least one of a previously measured EBL of the subject, a previously measured hemoglobin concentration of the fluid sample, a previously measured volume of the fluid sample, a volume of the container (e.g., canister) in which the fluid sample is positioned, the rate of IV fluid (or other fluid) administration, the sex of the subject, the weight of the subject, the age of the subject, and the like. Optionally, it is contemplated that the processor 200 can be positioned in operative communication with a user interface that is configured to receive the one or more inputs from a user. In exemplary aspects, the display and/or user interface can be secured to or defined thereon a portion of the device 10.

In one exemplary aspect, the processor 200 can be operatively coupled to the at least one photodetector 30. In this aspect, the processor 200 can be configured to receive the first and second signals from the at least one photodetector 30. Based upon the received first and second signals, the processor 200 can be configured to determine the concentration of hemoglobin within the fluid sample 12. Optionally, in some aspects, the processor 200 can be configured to visually depict the determined hemoglobin concentration of the fluid sample on a display positioned in operative communication with the processor.

Optionally, in exemplary aspects, following determination of the hemoglobin concentration within the fluid sample, at least a portion of the blood measurement device 10 can be configured to be discarded with the fluid sample (and, optionally, the container in which the fluid sample was positioned). In other exemplary aspects, it is contemplated that at least a portion of the blood measurement device 10 can be reusable (i.e., configured for multiple uses). Optionally, in some exemplary aspects, the entire blood measurement device 10 can be reusable.

In other exemplary aspects, the at least one photodetector 30 can comprise an array of a plurality of photodetectors. It is contemplated that the at least one photodetector 30 can comprise from about 1 photodetector to about 80 photodetectors. However, it is understood that any selected number of photodetectors can be used as disclosed herein. It is further contemplated that, in a blood loss measurement device 10 configured to measure volume, the at least one photodetector 30 can comprise at least 10 photodetectors. In exemplary aspects, it is contemplated that the array of photodetectors 30 can be radially spaced from the light source 40 by a distance ranging from about 0.05 mm to about 0.2 mm.

In other exemplary aspects, the light source 40 can comprise at least one light-emitting diode (LED) 42. In exemplary aspects, the at least one LED 42 can comprise from about 1 LED to about 160 LEDs. It is contemplated that, when the blood loss measurement device 10 is configured to measure a volume of the fluid sample 12, the at least one LED 42 can comprise at least 10 LEDs. In exemplary aspects, it is contemplated that at least one LED 42 can be configured to emit light at the first wavelength and at least one LED can be configured to emit light at the second wavelength. Alternatively, it is contemplated that at least one LED 42 can be configured to selectively emit light at both the first and second wavelengths. It is further contemplated that each LED 42 of the at least one LED can be configured for selective activation. When the at least one LED 42 comprises a plurality of LEDs, it is contemplated that the LEDs can be provided in the form of an array. Optionally, the plurality of LEDs 42 can be positioned in substantial alignment within a single row, and the row can be oriented substantially parallel to a vertical axis 21.

Figure 2:
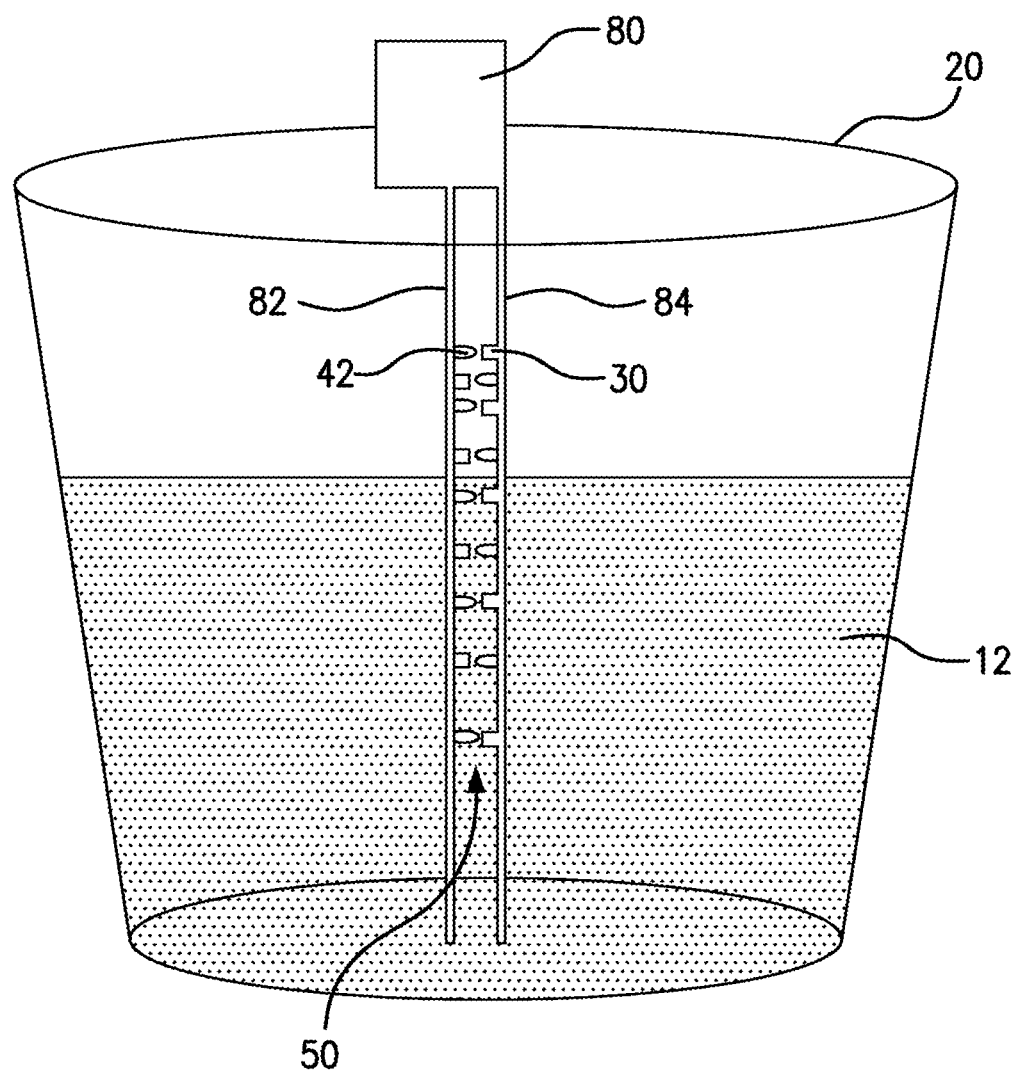
FIG. 2 depicts another exemplary blood measurement system as disclosed herein, showing a base element having first and second members.

In various aspects, and as shown in FIG. 2, the blood measurement device 10 can further comprise a base element 80 configured for selective insertion within the fluid sample 12. Optionally, in these aspects, it is contemplated that the light source 40 can be operatively coupled to the base element 80, and the base element 80 and the light source 40 can be configured for selective insertion within the fluid sample as a unitary structure. Alternatively, it is contemplated that the at least one photodetector 30 can be operatively coupled to the base element 80, and the base element and the at least one photodetector can be configured for selective insertion within the fluid sample as a unitary structure. In exemplary aspects, it is contemplated that first and second base elements 80 can be provided, with the first base element being operatively coupled to the light source 40 and the second base element being operatively coupled to the at least one photodetector 30. Thus, in use, the base element 80 (or base elements) can function as a dipstick-type element that can be selectively placed into a fluid sample to permit generation of light at the first and second wavelengths by the light source 40 and/or measurement of absorbance by the at least one photodetector 30 as disclosed herein. In additional aspects, and as further described herein, the base element 80 can be configured for selective attachment to a suction canister 20 or other container in which the fluid sample is positioned.

In some optional aspects, and with reference to FIG. 2, the base element 80 can have first and second opposed members 82, 84. In these aspects, the first and second opposed members 82, 84 can at least partially define a sample chamber 50 configured to receive a portion of the fluid sample. In exemplary aspects, the light source 40 can be operatively coupled to the first member 82 of the base element 80, and the at least one photodetector 30 can be operatively coupled to the opposed second member 84 of the base element. Alternatively, in other exemplary aspects, when the light source 40 comprises a plurality of LEDs 42 and the at least one photodetector comprises a plurality of photodetectors 30, it is contemplated that the LEDs and the photodetectors can be provided in an alternating pattern along a length of each of the first member 82 and the second member 84. In these aspects, the LEDs 42 and photodetectors 30 can be coupled to the first and second members 82, 84 such that each photodetector is positioned radially across from a corresponding LED. Optionally, in use, it is contemplated that the base element 80, the light source 40, and the at least one photodetector 30 can be configured for selective insertion within the fluid sample as a unitary structure. In exemplary aspects, the first and second opposed members 82, 84 can be spaced from one another by a distance ranging from about 0.05 mm to about 0.2 mm, thereby maintaining the desired spacing between the light source 40 and the at least one photodetector 30.

In some exemplary aspects, it is contemplated that the base element 80 and any other components of the device 10 that are operatively coupled to the base element can be reusable (i.e., configured for multiple uses). Thus, in these aspects, it is contemplated that the base element 80 can be inserted into a first fluid sample to permit measurement of the hemoglobin concentration of the first fluid sample, removed from the first fluid sample, and then inserted into a second fluid sample to permit measurement of the hemoglobin concentration of the second fluid sample.

In further exemplary aspects, the blood measurement device 10 can further comprise a plurality of pairs of opposed optical fibers 90. In these aspects, each pair of optical fibers can comprise a first optical fiber 90a operatively coupled to a corresponding LED 42 of the plurality of LEDs and a second optical fiber 90b operatively coupled to a corresponding photodetector 30 of the plurality of photodetectors. It is contemplated that the plurality of pairs of opposed optical fibers 90 can be configured for selective insertion within the fluid sample. In the operative position, it is contemplated that the plurality of photodetectors 30 and the plurality of LEDs 42 will not be in fluid communication with (i.e., do not contact) the fluid sample. In exemplary aspects, the plurality of pairs of opposed optical fibers 90 can be selectively detachable from at least one of the light source 40 (LEDs 42) and the at least one photodetector 30.

In additional aspects, it is contemplated that each optical fiber of the plurality of pairs of opposed optical fibers can comprise a receiving end 92 and an opposed transmitting end 94. In these aspects, the receiving end 92a of the first optical fiber 90a of each pair of optical fibers can be configured to receive light from a corresponding LED of the plurality of LEDs, the transmitting end 94a of the first optical fiber of each pair of optical fibers can be configured to transmit the received light (from the LED) within the fluid sample, the receiving end 92b of the second optical fiber 90b of each pair of optical fibers can be configured to receive light transmitted by the transmitting end 94a of an opposed first optical fiber (and that is not absorbed by the fluid sample), and the transmitting end 94b of the second optical fiber of each pair of optical fibers can be configured to transmit the received light (from the receiving end 92b) to a corresponding photodetector 30 of the plurality of photodetectors. In exemplary aspects, the transmitting end 94a of the first optical fiber 90a of each pair of optical fibers can be spaced from the receiving end 92b of a corresponding second optical fiber 90b by a selected distance. In these aspects, it is contemplated that the selected distance can range from about 0.05 mm to about 0.2 mm.

In one exemplary aspect, the processor 200 can be configured to determine the concentration of hemoglobin within the fluid sample based upon the equation:

$$Hgb = (A_1 - A_2) * k_1 + k_2, \text{ where:}$$

Hgb=the total hemoglobin concentration within the fluid sample;
$A_1$=the measured absorbance of the light within the fluid sample at the first wavelength;
$A_2$=the measured absorbance of the light within the fluid sample at the second wavelength;
$K_1$=the calibration coefficient for light at the first wavelength; and
$K_2$=the calibration coefficient for light at the second wavelength.

In additional exemplary aspects, the processor 200 can be configured to receive at least one input indicative of a volume of the sample fluid. In these aspects, it is contemplated that a user of the blood measurement device 10 can provide an input corresponding to the volume of the sample fluid. Alternatively, it is contemplated that the blood measurement device 10 can be configured to determine the volume of the sample fluid.

In one exemplary aspect, when the at least one photodetector 30 comprises an array of a plurality of photodetectors, the photodetectors of the array of photodetectors can be spaced relative to a vertical axis 21 that is in alignment with the directional force of gravity. In these aspects, each photodetector 30 of the array of photodetectors can be configured to produce a transmittance signal indicative of the transmittance of light measured by the photodetector. It is contemplated that the processor 200 can be configured to receive the transmittance signal from each photodetector 30. It is further contemplated that the processor 200 can be configured to associate the transmittance signal produced by each respective photodetector 30 of the array of photodetectors with a position of the photodetector relative to the vertical axis 21. It is still further contemplated that the processor 200 can be configured to determine the highest position at which a photodetector 30 of the array of photodetectors produced a transmittance signal indicative of a transmittance of less than 100%. In operation, it is contemplated that the highest position at which a photodetector 30 of the array of photodetectors produced a transmittance signal indicative of a transmittance of less than 100% can correspond to the height of the fluid sample. It is further contemplated that the processor 200 can be configured to determine the volume of the fluid sample based upon the height of the fluid sample. In exemplary aspects, it is contemplated that a user can input information describing the dimensions, shape, and/or orientation of the container in which the fluid sample is positioned, thereby permitting the processor to determine the volume of the fluid sample based upon the height of the fluid sample.

In still other exemplary aspects, it is contemplated that each photodetector 30 of the array of photodetectors can be configured to detect the transmittance of light at a respective position relative to the vertical axis 21. In exemplary aspects, it is contemplated that the photodetectors 30 can be spaced relatively farther apart proximate a bottom portion of the fluid sample and can be spaced relatively closer together proximate a top portion of the fluid sample. In exemplary aspects, when the fluid sample is positioned within a suction canister 20, it is contemplated that the photodetectors 30 can be spaced relatively farther apart proximate a bottom surface of the suction canister and can be spaced relatively closer together proximate a top opening of the suction canister, thereby ensuring that the volume of the fluid sample can be accurately assessed in a truncated cone-shaped canister.

In various aspects, the processor 200 can be configured to determine the volume of blood within the fluid sample. In exemplary aspects, the processor 200 can be used to determine the blood loss of a subject during a medical procedure. In one exemplary aspect, the processor 200 can be configured to determine the volume of blood within the fluid sample according to the equation:

$$EBL(t)=EBL(t-1)+[V_C(t)-V_C(t-1)]*[Hgb_C(t)/Hgb_P(t-1)], \text{ where:}$$

EBL(t)=Estimated Blood Loss at current time (t);
EBL(t−1)=Estimated Blood Loss at previously measured time (t−1);
$V_C$(t−1)=Volume of Fluid Sample within Suction Canister at previously measured time (t−1);
$Hgb_C$(t)=Hemoglobin Concentration of Fluid Sample within Suction Canister at current time (t); and
$Hgb_P$(t−1)=Hemoglobin Concentration of Blood as it Left the Subject at previously measured time (t−1).

In exemplary optional aspects, it is contemplated that the subject's hemoglobin at previously measured time (t−1) can correspond to one of: the subject's preoperative hemoglobin concentration; an updated hemoglobin concentration of the subject, determined from a subject's blood sample; an updated hemoglobin concentration of the subject, based upon an estimate provided by a practitioner (e.g., an anesthesiologist); or an updated hemoglobin concentration of the subject, based upon a continuous, non-invasive method as is known in the art. It is contemplated that, when an updated hemoglobin concentration of the subject is determined, the preoperative hemoglobin concentration of the subject can be averaged with the updated hemoglobin concentration to obtain the subject's hemoglobin at previously measured time (t−1).

Figure 1:
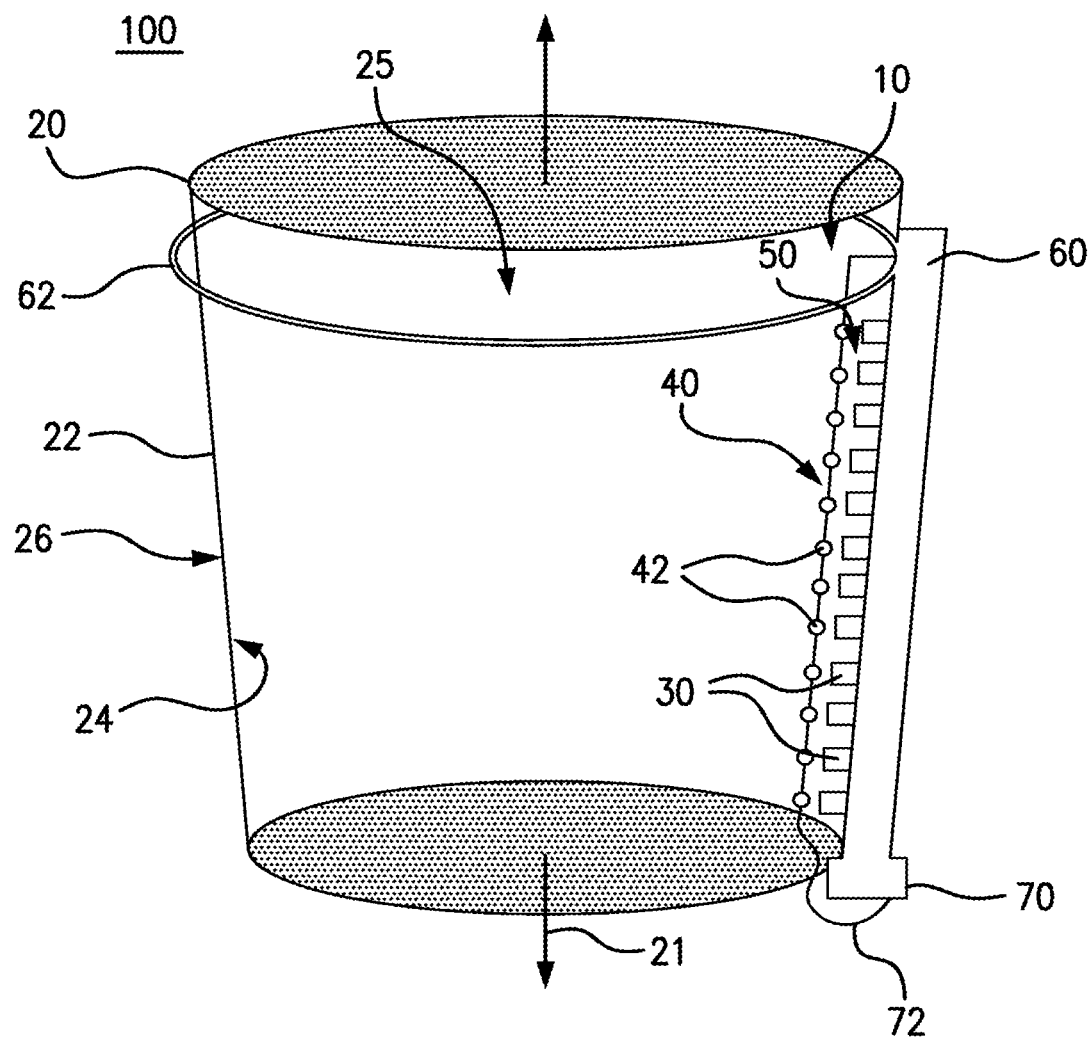
FIG. 1 depicts an exemplary blood measurement system as disclosed herein.

In a further aspect, the blood measurement device 10 can comprise a power source 70 positioned in operative communication with the at least one photodetector 30 and the light source 40. In exemplary aspects, as shown in FIG. 1, the power source 70 can be positioned in operative communication with the at least one photodetector 30 and the light source 40 through conventional wiring 72. Alternatively, it is contemplated that the power source 70 can provide power through wireless transmission means as are known in the art. It is contemplated that the power source 70 can be any conventional power source as is known in the art. In exemplary aspects, the power source can comprise a battery. In other exemplary aspects, it is contemplated that the power source can comprise a DC power source. In still other exemplary aspects, it is contemplated that the power source can comprise an AC power source.

In use, and as schematically depicted in FIG. 4, it is contemplated that the blood measurement device 10 can optionally be configured to create a feedback loop at any given time between the calculated patient hemoglobin concentration and the hemoglobin concentration and volume of the sample fluid, thereby resulting in a continuous display of estimated patient blood loss. As depicted in FIG. 5, after the blood measurement device 10 calculates the estimated blood loss and the updated patient hemoglobin concentration based on the data output from the photodetectors 30 as disclosed herein, it is contemplated that the results can be transmitted to a memory and/or display that are in communication with the processor 200. As further disclosed herein, it is contemplated that patient hemoglobin concentration data can be determined using conventional methods and provided manually as an input to the processor 200.

Blood Measurement System

In exemplary aspects, and with reference to FIGS. 1-6, the blood measurement system 100 can comprise the blood measurement device 10 and a container, such as, for example and without limitation, a suction canister 20. Although described herein as a suction canister, it is contemplated that the container can be any conventional container that is configured to receive a fluid sample. For example, in exemplary aspects, it is contemplated that the container can be a cell saver, which is configured to clean a fluid sample to permit delivery of the fluid sample to a patient.

In one aspect, the suction canister 20 can have a central axis that, during use, is generally axially aligned with the vertical axis 21. In one aspect, the suction canister 20 can have a wall 22 with an internal surface 24 and an external surface 26. The internal surface 24 of the suction canister 20 can define an interior space 25 of the suction canister. It is contemplated that the interior space 25 of the suction canister 20 can be configured to receive the fluid sample 12. In exemplary aspects, the suction canister 20 can comprise conventional plastic materials, including, for example and without, transparent plastic materials. In further exemplary aspects, it is contemplated that the suction canister 20 can be provided with volume measurement lines and other measurement lines and markings as are conventionally known in the art.

It is contemplated that the suction canister 20 can be configured for operative coupling to one or more sections of suction tubing as are conventionally used during surgical procedures to facilitate transport of bodily fluids and/or irrigation fluids to the suction canister. It is further contemplated that the suction canister 20 can have any conventional shape, including, for example and without limitation, a substantially cylindrical shape. It is still further contemplated the suction canister 20 can have any selected dimensions. In exemplary aspects, it is contemplated that the suction canister 20 can have a volume ranging from about 0.5 Liter to about 5 Liters.

In exemplary aspects, it is contemplated that the canister 20 can define one or more receptacles that are configured to receive at least a portion of the light source 40. It is further contemplated that the canister 20 can further define one or more receptacles that are configured to receive at least a portion of the at least one photoreceptor 30. It is still further contemplated that the receptacles in which the light source 40 and the at least one photoreceptor are received can be positioned to receive the light source and the at least one photoreceptor in the operative position, as further disclosed herein. In further exemplary aspects, it is contemplated that the canister 20 can define one or more receptacles that are configured to receive portions of a base element 80 as disclosed herein. When the base element comprises first and second members 82, 84 as disclosed herein, it is contemplated that the canister 20 can define a first receptacle configured to receive a portion of the first member 82 and a second receptacle configured to receive a portion of the second member 84, with the first and second receptacles being spaced to maintain a desired separation between the light source 40 and the at least one photoreceptor 30.

In further exemplary aspects, the canister 20 can comprise a lid configured to enclose a top opening of the canister. In these aspects, it is contemplated that the lid of the canister 20 can define at least one opening configured to receive one or more portions of the blood measurement device 10, including, for example and without limitation, the light source 40, the at least one photodetector 30, an optical fiber 90, and the wiring 72. In one exemplary aspect, when the at least one photodetector 30 and the light source 40 are positioned in the operative position, it is contemplated that at least a portion of the wiring 70 can be positioned within the interior space 25 of the canister 20. In this aspect, it is further contemplated that when the at least one photodetector 30 and the light source 40 are positioned in the operative position, at least a portion of the wiring 70 can be positioned outside the interior space 25 of the canister 20 and, optionally, can be positioned externally to the canister.

Optionally, it is contemplated that the at least one photodetector 30 and the light source 40 can be selectively operatively coupled to the wall 22 of the suction canister 20. However, in some aspects, it is contemplated that the at least one photodetector 30 and/or the light source 40 can optionally be positioned within a central portion of the interior space 25 of the suction canister 20 (and radially spaced from the wall 22 of the suction canister). In still other aspects, and as further disclosed herein, it is contemplated that the at least one photodetector 30 and/or the tight source 40 can be secured to a base element 80 that is configured for selective insertion within the sample fluid within the suction canister 20.

In a further aspect, as further disclosed herein, the blood measurement device 10 can comprise a sample chamber 50 positioned within the interior space 25 of the suction canister 20. Generally, the sample chamber 50 corresponds to the three-dimensional volume defined between the light source 40 and the at least one photodetector 30. Thus, it is contemplated that the sample chamber 50 can be configured to receive a portion of the fluid sample within the interior space 25 of the suction canister 20. The radial dimension of the sample chamber 50 can generally correspond to the distance light at the first and second wavelengths can travel in whole blood and, generally, can range from about 0.05 mm to about 0.20 mm, as further disclosed herein. In exemplary aspects, the sample chamber 50 can be at least partially open on two opposed sides to facilitate fluid diffusion and mixing of the fluid sample. In exemplary aspects, it is contemplated that the sample chamber 50 can have a width (measured circumferentially at a selected radial distance from the central axis (shown in substantial alignment with vertical axis 21) of the canister 20) ranging from about 2 to about 15 mm. It is further contemplated that, in exemplary aspects, the width of the sample chamber 50 can be about 5 mm.

In exemplary aspects, it is contemplated that one or more components of the blood measurement device 10 can be integrally formed with the canister 20. For example, in some aspects, the at least one photodetector 30 can be integrally formed with the wall 22 of the canister 20. In these aspects, it is contemplated that the at least one photodetector 30 can be connected to the internal surface 24 or external surface 26 of the wall 22 of the suction canister 20 such that the at least one photodetector 30 can receive light from within the canister. In further exemplary aspects, it is contemplated that the light source 40 can be integrally formed with the wall 22 of the canister 20. In these aspects, it is contemplated that the light source 40 can be mounted to the internal surface 24 or external surface 26 of the wall 22 of the suction canister 20 such that the light source can transmit light into the canister. In various exemplary aspects, it is contemplated that at least a portion of the wiring 72 of the blood measurement device 10 can be positioned within the wall 22 of the suction canister 20. In further exemplary aspects, it is contemplated that at least a portion of the optical fibers 90 disclosed herein can be integrally formed (for example, embedded within) the wall 22, bottom portion, and/or lid of the canister 20. Optionally, in exemplary aspects, it is contemplated that the at least one photodetector 30 can comprise at least one bio-chemical receptor affixed to the internal surface 24 of the wall 22 of the suction canister 20.

Optionally, in further aspects, it is contemplated that light-transmitting paint or film (i.e., paints or films that permit transmission of light) as are known in the art can be selectively applied to portions of the wall 22 of the suction canister 20 and/or portions of the blood measurement device to permit transmission of light within and through canister 20. In these aspects, it is contemplated that, in the operative position, at least one of the light source 40 and the at least one photodetector 30 can be positioned out of fluid communication with (i.e., not contact) the fluid sample. For example, when portions of the wall 22 of the suction canister 20 are provided with light-transmitting paint or film, it is contemplated that the light source 40 can be configured for positioning within the fluid sample and the at least one photodetector 30 can be positioned external to the canister but proximate to the wall of the canister such that each photodetector is configured to receive light transmitted through the light-transmitting paint or film. Alternatively, it is contemplated that the light source 40 can be configured for positioning proximate the portions of the wall provided with light-transmitting paint or film such that the light-transmitting material of the canister receive at least a portion of the light transmitted by the light source, and the at least one photodetector 30 can be configured for positioning within the canister proximate the wall of the canister such that each photodetector is positioned to receive light transmitted through the light-transmitting material. In additional exemplary aspects, it is contemplated that light-transmitting paint or film can be selectively applied to portions of a base element 80 as disclosed herein. For example, it is contemplated that at least one of the first and second members 82, 84 of a base element can be provided with light-transmitting material in selected areas.

Optionally, in some aspects, the blood measurement system 100 can comprise a housing 60 configured to receive at least a portion of the suction canister 20. In these aspects, the housing 60 can optionally comprise a frame 62 that is configured to surround at least a portion of the wall 22 of the suction canister 20. It is contemplated that the housing 60 can be configured to support and/or stabilize the suction canister 20 in an operative position during a medical procedure. In exemplary aspects, the power source 70 can be positioned within and/or coupled to the housing 60.

Optionally, it is contemplated that the blood measurement system 10 can comprise a stirrer positioned within the interior space 25 of the suction canister 20. In exemplary aspects, the stirrer can be a magnetic stirrer as is known in the art. However, it is contemplated that the stirrer can be any conventional stirrer as is known in the art. It is further contemplated that the stirrer can be configured for selective activation. In exemplary aspects, it is contemplated that the stirrer can be positioned proximate the bottom surface of the suction canister 20.

Optionally, in another exemplary aspect, the blood measurement system 100 can further comprise a drip counter 150 configured for communication with an intravenous (IV) fluid delivery element, such as, for example and without limitation, an IV bag as is known in the art. In this aspect, the drip counter 150 can be configured to produce a volume signal indicative of the volume of IV fluid dispensed from the IV fluid delivery element and/or a delivery rate signal indicative of the rate at which IV fluid is dispensed from the IV fluid delivery element. It is contemplated that the drip counter 150 can be positioned in operative communication with the processor 200 such that the processor is configured to receive the volume signal and/or the delivery rate signal. Alternatively, the volume and/or rate information can be entered manually by a user of the disclosed system 100.

In further exemplary aspects, it is contemplated that the blood measurement system can optionally comprise a plurality of blood measurement devices that have a common processor or, alternatively, that have discrete processors that are in operative communication with each other. In these aspects, it is further contemplated that the blood measurement system can comprise a plurality of containers (e.g., a plurality of suction canisters 20), with a blood measurement device being configured for selective positioning relative to a respective container. It is contemplated that such a configuration can permit determination of comprehensive blood loss information in circumstances when more than one container is used to collect fluids during a single medical procedure.

Methods of Determining Blood Loss

In use, the disclosed blood measurement devices and systems 10, 100 can be used to measure the amount of blood within a fluid sample. In exemplary aspects, the disclosed blood measurement devices and systems 10, 100 can be used to measure the blood loss of a subject during a medical procedure, such as, for example and without limitation, a surgical procedure. As set forth herein, it is contemplated that the blood measurement devices and systems 10, 100 can be configured to repeatedly measure the hemoglobin concentration of the fluid sample within a suction canister 20, as well as the volume of the sample fluid within the suction canister. Throughout the medical procedure, it is contemplated that the blood measurement device 10 can be configured to export these measurements to the processor 200, which can use the measurements, along with the updated concentration of the subject's hemoglobin concentration, to calculate the volume of blood in the suction container 20. Thus, a method of measuring the amount of blood of a subject within a fluid sample (e.g., determining the blood loss of the subject) can comprise operatively positioning the blood measurement device relative to the fluid sample and using the blood measurement device to determine the concentration of hemoglobin within the fluid sample. More specifically, the method can comprise positioning the light source and the at least one photodetector in the operative position relative to the fluid sample. With the light source and the at least one photodetector positioned in the operative position, the method can further comprise selectively activating the light source to sequentially generate light at the first and second wavelengths. The method can further comprise receiving the transmitted light using the at least one photodetector. The method can still further comprise, through the processor, receiving the first and second output signals of the at least one photodetector and determining the hemoglobin concentration within the fluid sample. In further exemplary aspects, the method can comprise, through the processor, determining the volume of blood within the fluid sample. In still further exemplary aspects, the method can comprise, through the processor, determining the volume of the fluid sample. Alternatively, it is contemplated that the method can comprise, through the processor, receiving an input indicative of the volume of the fluid sample. In further exemplary aspects, the method can optionally comprise, through the processor, receiving an input indicative of a starting (or other previously measured) hemoglobin concentration of the subject.

In exemplary aspects, the hemoglobin concentration of the fluid sample within the suction container 20 can be measured through one or more hemoglobinometry techniques as are known in the art. Generally, these known color or light-intensity matching techniques can be used to measure the concentration of methemoglobin or sulphemoglobin, which provide an indication of the overall hemoglobin concentration of the fluid sample within the suction canister 20. Thus, in various aspects, the method of measuring the amount of blood of a subject within a fluid sample (e.g., determining the blood loss of the subject) can optionally comprise administering one or more reagents to the fluid sample. In these aspects, the one or more reagents can be configured to convert hemoglobin within the fluid sample into one of methemoglobin and sulphemoglobin. In exemplary aspects, the fluid sample can optionally be positioned within a suction canister 20 as disclosed herein, and the one or more reagents can be added to the suction canister. In some exemplary aspects, it is contemplated that the one or more reagents (and/or a solution containing such reagents) can be administered to the internal surface 24 of the wall 22 of the suction canister 20. In other exemplary aspects, it is contemplated that the one or more reagents can be added to the suction canister 20 (or other container) before the fluid sample is received within the suction canister (or other container). In further exemplary aspects, it is contemplated that the one or more reagents can be applied to selected surfaces of the blood measurement device 10 that are configured for positioning within the fluid sample. In these aspects, it is contemplated that the one or more reagents can be configured to circulate within the fluid sample following contact between the selected surfaces of the blood measurement device 10 and the fluid sample. Optionally, in one exemplary aspect, selected surfaces of a base element 80 as disclosed herein can be coated with the one or more reagents.

In some aspects, the reagents (and/or the solution containing the reagents) can be allowed to air-dry. Alternatively, in other aspects, the reagents (and/or a solution containing such reagents) can be provided at a predetermined concentration such that dilution of the reagents and/or solution by the fluid sample can yield a desired reagent concentration.

An exemplary method for measuring the methemoglobin concentration within the fluid sample comprises the use of hemiglobincyanide (HiCN; cyanmethamoglobin) as a reagent. The use of hemiglobincyanide as a reagent is described in Zijlstra W G, Van Kampen E. Standardization of hemoglobinometry. I. The extinction coefficient of hemiglobincyanide. Clin Chim Acta. 1960 September; 5:719-26, which is incorporated herein by reference in its entirety. Alternatively, in one exemplary aspect, the reagent can comprise sodium azide or sodium lauryl sulphate, which convert the hemoglobin to azidmethemiglobin and hemiglobinsulphate, respectively. Exemplary methods of measuring hemoglobin within the blood using sodium azide are described in Vanzetti G. An azide-methemoglobin method for hemoglobin determination in blood. J Lab Lab Clin Med. 1966 January; 67(1):116-26, which is hereby incorporated herein by reference in its entirety. Exemplary methods of measuring hemoglobin within the blood using sodium lauryl sulphate are described in Oshiro I, Takenaka T, Maeda J. New method for hemoglobin determination by using sodium lauryl sulfate (SLS). Clin Biochem. 1982 April; 15(2):83-8, and in Lewis S M, Garvey B, Manning R, Sharp S A, Wardle J. Lauryl sulphate haemoglobin: a non-hazardous substitute for HiCN in haemoglobinometry. Clin Lab Haematol. 1991; 13(3):279-90, both of which are hereby incorporated herein by reference in their entirety. Optionally, in some aspects, it is contemplated that one or more lysing agents can be added to the solvent. Exemplary lysing agents can be selected from the group consisting of desoxycholate, quaternary ammonium salts, and quaternary ammonium surfactants, such as, for example and without limitation, anionic, non-ionic, zwitterionic, and cationic surfactants. In one exemplary aspect, the following compositions can be added per liter of solvent: 40 g sodium desoxycholate (to lyse the cells within the fluid sample); 20 g sodium nitrite (to convert the hemoblogin iron from ferrous to ferric state); and 18 g sodium azide (to form azidmethemoglobin).

Optionally, in various exemplary aspects, the method of measuring the amount of blood of a subject within the fluid sample can further comprise delivering an anti-coagulant to the fluid sample. In these aspects, it is contemplated that the method of measuring the amount of blood of the subject within the fluid sample can comprise delivering a desired amount of anti-coagulant for each liter of fluid sample that is collected within the suction canister 20 or other container. In exemplary aspects, the anti-coagulant can be Heparin. In these aspects, it is contemplated that the method of measuring the amount of blood of the subject within the fluid sample can comprise delivering a selected number of units of Heparin for each liter of fluid sample that is collected within the suction canister 20 or other container. For example, it is contemplated that that the selected number of units of Heparin can be about 20,000 units of Heparin per liter of fluid sample. However, it is contemplated that any conventional anti-coagulant drug can be delivered in a selected quantity relative to the volume of the fluid sample. For example, it is contemplated that the anti-coagulant can be selected from the group consisting of Ethylenediaminetetraacetic acid (EDTA) and Citrate. Optionally, in some applications, it is contemplated that a plurality of anti-coagulants can be delivered to the fluid sample. In further exemplary aspects, it is contemplated that the anti-coagulant or plurality of anti-coagulants can be provided to the fluid sample in any form, including, for example and without limitation, liquid or solid forms. Typically, it is contemplated that the anti-coagulants) can be delivered using a syringe as is conventional in the art. However, it is contemplated that any suitable delivery method can be used. In one exemplary aspect, it is contemplated that a solid form of the anti-coagulant can be fixedly coupled to the internal surface of a suction canister such that the anti-coagulant contacts the fluid sample as it fills up the suction canister. In another exemplary aspect, it is contemplated that a solid form of the anti-coagulant can be fixedly coupled to selected portions of a base element 80 as disclosed herein such that the base element can be selectively inserted within the fluid sample to provide the anti-coagulant to the fluid sample.

In methods in which anti-coagulants are not provided to the fluid sample, it is contemplated that absorbance data obtained when the fluid sample first enters the canister or other container should be used in determining the hemoglobin concentration, whereas the absorbance data obtained following coagulation of the blood within the fluid sample should be disregarded. Thus, it is contemplated that the processor can be configured to disregard absorbance data obtained following coagulation of blood within the fluid sample. Alternatively, the method can comprise inserting the light source and the at least one photodetector into the fluid sample before coagulation of the blood within the fluid sample has occurred and removing the light source and the at least one photodetector from the fluid sample and/or ceasing activation of the light source and at least one photodetector after coagulation of the blood within the fluid sample has occurred.

In further aspects, upon application of light from the light source 40, the sample fluid within the suction canister 20 can be analyzed using the at least one photodetector 30 disclosed herein. Optionally, it is contemplated that the LEDs configured to emit light at the first wavelength and the LEDs configured to emit light at the second wavelength can be activated in an alternating pattern to permit the at least one photodetector 30 to measure the absorbance of the sample fluid at each wavelength. It is further contemplated that the LEDs can be turned off to assess the ambient light of the room.

When a base element 80 as disclosed herein is used, it is contemplated that the disclosed method can comprise selectively positioning the base element within the fluid sample and, after positioning the base element within the fluid sample, selectively activating the light source to transmit light to the at least one photodetector.

Before the intraoperative patient blood loss of a subject can be determined, the blood volume in the suction canister must first be determined. During the course of a surgical procedure, it is contemplated that fluid can collect in the suction canister, with some portion of the fluid being blood of the subject. The fluid sample within the suction canister can have a hemoglobin concentration, Hgbc, which will vary with time. The equivalent volume of blood for this hemoglobin concentration can determined by the hemoglobin of the blood, as measured when the blood left the patient (subject), Hgbp(t), which also varies with time. To facilitate conversion of these equations to an iterative algorithm that is updated at each measurement, it is contemplated that t can represent the current time and, thus, t−1 can represent the most recent measurement time.

With these conventions, the subject's estimated blood loss (EBL) for each measurement of the suction canister fluid hemoglobin can be determined according to the following equation (1), as further described herein:

$$EBL(t)=EBL(t-1)+[Vc(t)-Vc(t-1)]*(Hgbc(t)/Hgbp(t-1)) \quad (1)$$

where Vc is the volume of fluid in the suction canister and EBL is the time varying measure of the subject's cumulative blood loss.

It is contemplated that the measurement of patient hemoglobin, Hgbp, at regular intervals can be a challenge because it requires that a subject's blood sample be obtained. In exemplary aspects, the method of estimating the blood loss of a subject can comprise estimating the value of Hgbp. It is contemplated that the estimated blood volume (EBV) of a patient under normal, preoperative conditions can be approximated from the patient's sex, height and weight. It is further contemplated that this EBV value can be updated by tracking the addition of IV fluids ($V_{IV}$) and the blood loss (EBL). It is contemplated that the derivation of this technique can begin with the following iterative equation (2) for adjusting the estimated blood volume:

$$EBV(t) \approx EBV(t-1) + [V_{IV}(t) - V_{IV}(t-1)] - [EBL(t) - EBL(t-1)] \quad (2)$$

The conservation of total hemoglobin from one time to the next can then be expressed by setting the total hemoglobin at any time as being equal to the sum of the total patient hemoglobin and the total suction canister fluid hemoglobin, i.e., the system consisting of the patient's blood and the suction canister blood is closed and thus total hemoglobin (although not hemoglobin concentration) is conserved at all times. It is contemplated that this approximation can be expressed as equation (3):

$$EBV(t-1)*Hgbp(t-1) = EBV(t)*Hgbp(t) + [Vc(t) - Vc(t-1)]*Hgbc(t) \quad (3)$$

where the first term on the right hand side is the total hemoglobin of the patient at time t and the second term is the total hemoglobin that has entered the suction canister over the time from t−1 to t.

Reorganizing this equation in terms of the Hgbp, it becomes equation (4):

$$Hgbp(t) = (EBV(t-1)*Hgbp(t-1) - [Vc(t) - Vc(t-1)]*Hgbc(t))/EBV(t) \quad (4)$$

This expression, combined with Equation 2 above, can provide the basis for an iterative algorithm to update the estimate of the patient hemoglobin based on ongoing measurements of volume and hemoglobin from the suction canister. Combining that result with Equation 1 then provides a means to estimate the cumulative blood loss in a patient (EBL). Alternatively, as further disclosed herein, it is contemplated that the patient hemoglobin concentration can optionally be determined manually using conventional methods and provided to the processor as one or more inputs.

In use, it is contemplated that the disclosed devices and systems can be configured to correlate hemoglobin and blood loss data with time. More particularly, it is contemplated that the processor of the disclosed devices and systems can be configured to associate the determined hemoglobin concentrations and estimated blood loss values with respective time points, to thereby permit evaluation of changes in these concentrations and values over time. It is further contemplated that these changes can be correlated with the period during which a medical procedure is performed and, thus, with specific events that occurred during the medical procedure. In exemplary applications, it is contemplated that the processor can be configured to determine the period during which one or more fluids entered a particular fluid sample. In another exemplary application, it is contemplated that the processor can be configured to produce an alert signal when one or more selected conditions are detected by the disclosed device. The processor can be further configured to cause alarm generation means to produce an audible and/or visible alarm in response to detection of the one or more selected conditions. The alarm generation means can optionally be provided in communication with a display and/or user interface as disclosed herein. In additional optional aspects, it is contemplated that the alarm generation means can comprise a speaker in communication with the processor. In exemplary aspects, the one or more selected conditions can comprise at least one of: detection of minimally diluted blood entering the canister at a determined rate; a predetermined volume of blood being collected within the canister in a particular time period; or a predetermined quantity of hemoglobin being collected within the canister in a particular time period.

Optionally, the methods disclosed herein can comprise collecting fluid samples in a plurality of containers and selectively positioning a blood measurement device relative to each respective container to thereby provide comprehensive hemoglobin and/or blood loss information based upon all of the fluid in the plurality of containers.

Although the blood measurement devices, systems, and methods disclosed herein are described herein as determining the amount of blood in the fluid sample based upon the concentration of hemoglobin within the fluid sample, it is contemplated that the amount of blood in the fluid sample can similarly be determined using other blood constituents, including, for example and without limitation, white blood cells (leukocytes), red blood cells (erythrocytes), platelets (thrombocytes), blood urea nitrogen, and serum creatinine. It is further contemplated that the equations disclosed herein can be modified to be based on the concentration of one of these blood constituents within the blood of the patient and within the fluid sample.

Experimental Example

The following example is put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

As shown in FIGS. 7 and 8, preliminary results for an exemplary blood measurement system's accuracy for estimation of patient hemoglobin during IV dilution and minimal blood loss showed $R^2$ of 0.80, bias of 0.20 g/dL and limits of agreement (bias±1.96 SD) of 0.20±1.39 g/dL. These results were observed for 21 surgery patients for whom the system's noninvasive estimates of hemoglobin concentration from equation (4) were compared to the actual changes in hemoglobin concentration as assessed invasively approximately once an hour before the surgery was complete.

Exemplary Aspects

In one exemplary aspect, a blood measurement device for determining the amount of blood of a subject within a fluid sample comprises: a light source configured to selectively generate light at a first wavelength and at a second wavelength different from the first wavelength; at least one photodetector, wherein the light source and the at least one photodetector are configured for positioning in an operative position, wherein, in the operative position, the at least one photodetector is configured to receive at least a portion of the light generated by the light source, and wherein upon positioning of the light source and the at least one photodetector in the operative position, the at least one photodetector is configured to produce a first signal indicative of the absorbance of the fluid sample at the first wavelength and a second signal indicative of the absorbance of the fluid sample at the second wavelength; and a processor operatively coupled to the at least one photodetector, wherein the processor is configured to receive the first and second signals from the at least one photodetector, and wherein, based upon the received first and second signals me of the fluid sample, the processor is configured to determine the concentration of hemoglobin within the fluid sample.

In another exemplary aspect, the first wavelength ranges from about 500 nm to about 600 nm, and the second wavelength ranges from about 850 nm to about 900 nm.

In another exemplary aspect, the first wavelength is about 525 nm, and the second wavelength is about 870 nm.

In another exemplary aspect, the blood measurement device further comprises a base element having first and second opposed members, and the first and second opposed members at least partially define a sample chamber configured to receive a portion of the fluid sample.

In another exemplary aspect, the light source is operatively coupled to the first member of the base element, and the at least one photodetector is operatively coupled to the opposed second member of the base element.

In another exemplary aspect, the base element, the light source, and the at least one photodetector are configured for selective insertion within the fluid sample as a unitary structure.

In another exemplary aspect, the base element is configured for selective attachment to a suction canister.

In another exemplary aspect, the blood measurement device further comprises a base element, and the light source is operatively coupled to the base element.

In another exemplary aspect, the base element and the light source are configured for selective insertion within the fluid sample as a unitary structure.

In another exemplary aspect, the base element is configured for selective attachment to a suction canister.

In another exemplary aspect, the at least one photodetector comprises an array of a plurality of photodetectors.

In another exemplary aspect, the light source comprises a plurality of light emitting diodes (LEDs), at least one LED of the plurality of LEDs is configured to emit light at the first wavelength, and at least one LED of the plurality of LEDs is configured to emit light at the second wavelength.

In another exemplary aspect, each LED of the plurality of LEDs is configured for selective activation.

In another exemplary aspect, the array of photodetectors is radially spaced from the light source by a distance ranging from about 0.05 mm to about 0.2 mm.

In another exemplary aspect, the blood measurement device further comprises a plurality of pairs of opposed optical fibers, each pair of optical fibers comprises a first optical fiber operatively coupled to a corresponding LED of the plurality of LEDs and a second optical fiber operatively coupled to a corresponding photodetector of the plurality of photodetectors, the plurality of opposed pairs of optical fibers are configured for selective insertion within the fluid sample, and in the operative position, the plurality of photodetectors and the plurality of LEDs are not in fluid communication with the fluid sample.

In another exemplary aspect, each optical fiber of the plurality of pairs of opposed optical fibers comprises a receiving end and an opposed transmitting end, the receiving end of the first optical fiber of each pair of optical fibers is configured to receive light from a corresponding LED of the plurality of LEDs, the transmitting end of the first optical fiber of each pair of optical fibers is configured to transmit received light within the fluid sample, the receiving end of the second optical fiber of each pair of optical fibers is configured to receive light transmitted by the transmitting end of an opposed first optical fiber, the transmitting end of the second optical fiber of each pair of optical fibers is configured to transmit the received light to a corresponding photodetector of the plurality of photodetectors, and the transmitting end of the first optical fiber of each pair of optical fibers is spaced from the receiving end of a corresponding second optical fiber by a selected distance.

In another exemplary aspect, the selected distance ranges from about 0.05 mm to about 0.2 mm.

In another exemplary aspect, the processor is configured to determine the concentration of hemoglobin within the fluid sample based upon the equation:

$$Hgb=(A_1-A_2)*k_1+k_2, \text{ where:}$$

$Hgb$=the total hemoglobin concentration within the fluid sample;

$A_1$=the measured absorbance of the light within the fluid sample the first wavelength;

$A_2$=the measured absorbance of the light within the fluid sample at the second wavelength;

$k_1$=the calibration coefficient for light at the first wavelength; and $k_2$=the calibration coefficient for light at the second wavelength.

In another exemplary aspect, the processor is configured to receive at least one input indicative of the volume of the sample fluid.

In another exemplary aspect, the plurality of photodetectors are spaced relative to a vertical axis, each photodetector of the array of photodetectors is configured to produce a transmittance signal indicative of the transmittance of light measured by the photodetector, and the processor is configured to receive the transmittance signal from each photodetector.

In another exemplary aspect, the processor is configured to associate the transmittance signal produced by each respective photodetector of the array of photodetectors with a position of the photodetector relative to the vertical axis, and the processor is configured to determine the highest position at which a photodetector of the array of photodetectors produced a transmittance signal indicative of a transmittance of less than 100%.

In another exemplary aspect, the highest position at which a photodetector of the array of photodetectors produced a transmittance signal indicative of a transmittance of less than 100% corresponds to the height of the fluid sample, and the processor is configured to determine the volume of the fluid sample based upon the height of the fluid sample.

In another exemplary aspect, the processor is configured to determine the volume of blood within the fluid sample according to the equations:

$$EBL(t)=EBL(t-1)+[V_C(t)-V_C(t-1)]*[Hgb_C(t)/Hgb_P(t-1)];$$

$$EBV(t) \approx EBV(t-1)+[V_{IV}(t)-V_{IV}(t-1)]-[EBL(t)-EBL(t-1)]; \text{ and}$$

$Hgbp(t)=(EBV(t-1)*Hgbp(t-1)-[Vc(t)-Vc(t-1)]$
$*Hgbc(t))/EBV(t)$, where:

EBL(t)=Estimated Blood Loss at current time (t);
EBL(t−1)=Estimated Blood Loss at previously measured time (t−1);
$V_C(t)$=Volume of Fluid Sample within Suction Canister at current time (t);
$V_C(t-1)$=Volume of Fluid Sample within Suction Canister at previously measured time (t−1);
$Hgb_C(t)$=Hemoglobin Concentration of Fluid Sample within Suction Canister at current time (t);
$Hgb_C(t-1)$=Hemoglobin Concentration of Fluid Sample within Suction Canister at previously measured time (t−1);
Hgbp(t)=Hemoglobin Concentration of Blood of the subject at current time (t);
Hgbp(t−1)=Hemoglobin Concentration of Blood as it Left the subject at previously measured time (t−1);
EBV(t)=Estimated Blood Volume of the subject at current time (t);
EBV(t−1)=Estimated Blood Volume of the subject at previously measured time (t−1);
$V_{IV}(t)$=Volume of IV Fluid within the subject at current time (t); and
$V_{IV}(t-1)$=Volume of IV Fluid within the subject at previously measured time (t−1).

In a further exemplary aspect, the processor can be configured to receive one or more user inputs, with each input corresponding to at least one of the following variables: Estimated Blood Loss (EBL) of the subject; Volume of the fluid sample; hemoglobin concentration of the blood of the subject; Estimated Blood Volume (EBV) of the subject; and volume of IV fluid administered to the subject.

In a further exemplary aspect, a blood measurement system comprises the blood measurement device of any one of the previously described aspects and a suction canister, the suction canister having an outer wall having an internal surface and an external surface, the internal surface of the outer wall defining an interior space configured to receive the fluid sample.

In another exemplary aspect, the light source is integrally formed with the suction canister.

In another exemplary aspect, the at least one photodetector is integrally formed with the suction canister.

In another exemplary aspect, the blood measurement system further comprises a drip counter configured for communication with an intravenous (IV) fluid delivery element, the drip counter is configured to produce a volume signal indicative of the volume of IV fluid dispensed from the IV fluid delivery element and a delivery rate signal indicative of the rate at which IV fluid is dispensed from the IV fluid delivery element, and the drip counter is positioned in operative communication with the processor such that the processor is configured to receive the volume signal and the delivery rate signal.

In another exemplary aspect, the processor is configured to receive at least one user input, and each user input is indicative of one of: a volume of one or more intravenous (IV) fluids dispensed from an IV fluid delivery element; and a rate at which the one or more IV fluids is dispensed from the TV fluid delivery element.

In an additional exemplary aspect, a method of measuring the amount of blood of a subject within a fluid sample comprises operatively positioning a blood measurement device of any of the preceding aspects relative to a fluid sample; and using the blood measurement device to determine the concentration of hemoglobin within the fluid sample.

In another exemplary aspect, the method further comprises administering one or more reagents to the fluid sample, wherein the one or more reagents are configured to convert hemoglobin within the fluid sample into one of methemoglobin and sulphemoglobin.

In another exemplary aspect, the method further comprises delivering an anti-coagulant to the fluid sample.

In another exemplary aspect, the anti-coagulant is heparin.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method of measuring an amount of hemoglobin over time in a fluid sample contained within a surgical suction container having a vertical axis, the method comprising:
measuring a hemoglobin concentration of a patient prior to a medical or surgical procedure;
operatively coupling the surgical suction container to a patient to receive fluid from the patient during the medical or surgical procedure, the surgical suction container including a blood measuring device comprising;
at least one light source, the at least one light source generating light directed into the surgical suction container at at least two different wavelengths;
at least one light detector, the at least one light detector positioned in an operative position with respect to the surgical suction container to receive at least a portion of the light generated by the at least one light source along at least a portion of a vertical axis of the surgical suction container, wherein the at least one light detector receives at least a portion of the light generated by the at least one light source and produces a first signal indicative of a first absorbance of light at a first wavelength by the fluid sample and a second signal indicative of a second absorbance of light at a second wavelength by the fluid sample; and
a processor operatively coupled to the at least one light detector, the processor receiving the first and second signals from the at least one light detector, and wherein, based upon the received first and second signals, the processor repeatedly determines a concentration of hemoglobin within the fluid sample as fluid from the subject is added to the fluid sample;
collecting fluid containing blood from the patient in the surgical suction container during the medical or surgical procedure with the at least one light detector submerged within the fluid sample;
receiving the first and second signals from the at least one light detector by the processor; and
repeatedly determining a real-time hemoglobin concentration with the processor based on the measured hemoglobin concentration of the patient and the first and second signals received from the at least one light detector;

measuring a real-time volume of fluid in the surgical suction container and providing the real-time volume of fluid in the surgical suction container to the processor; and using the real-time hemoglobin concentration of the fluid in the surgical suction container, the measured hemoglobin concentration of the patient and the real-time volume of fluid in the surgical suction container to determine a real-time blood volume in the surgical suction container.

2. The method of claim 1, further comprising delivering at least one reagent into the container, wherein the at least one reagent converts hemoglobin within the container into one of methemoglobin or sulphemoglobin.

3. The method of claim 1, further comprising delivering an anti-coagulant into the container.

4. The method of claim 1, wherein the at least one light detector detects light from the at least one light source at at least one of a plurality of locations along the vertical axis of the container.

5. The method of claim 1, wherein the at least one light source generates light at the at least two different wavelengths comprising light at a first wavelength and light at a second wavelength different from the first wavelength.

6. The method of claim 5, wherein the at least one light detector produces a first signal indicative of the first absorbance of light of the fluid sample at the first wavelength and a second signal indicative of the second absorbance of light of the fluid sample at the second wavelength.

7. The method of claim 1, wherein the at least one light source comprises a plurality of light emitting diodes (LEDs), wherein at least one LED of the plurality of LEDs is configured to emit light at the first wavelength, and wherein at least one LED of the plurality of LEDs is configured to emit light at the second wavelength, and wherein each LED of the plurality of LEDs is configured for selective activation by the processor.

8. A method of measuring blood loss of a patient over time during a medical or surgical procedure, comprising:

operatively coupling a suction canister to a patient having a medical or surgical procedure, the suction canister collecting fluid from the patient during the medical or surgical procedure, the fluid including blood of the patient, using a blood measuring device operatively coupled to the suction canister to measure an amount of blood of the patient contained within the fluid in the suction canister, the blood measuring device, comprising;

at least one light source configured to generate light at a first wavelength and at a second wavelength different from the first wavelength;

at least one light detector, wherein the at least one light source and the at least one light detector are configured for positioning in an operative position with respect to the container, wherein, in the operative position, the light source is configured to transmit light at a plurality of locations along a vertical axis of the container and the at least one light detector is configured to receive at least a portion of the light generated by the light source, and wherein upon positioning of the light source and the at least one light detector in the operative position, the at least one light detector is configured to produce a first signal indicative of a first absorbance of the fluid sample at the first wavelength and a second signal indicative of a second absorbance of the fluid sample at the second wavelength;

a volume measuring device configured to measure a real-time volume of fluid in the suction canister and provide the real-time volume of fluid in the suction canister; and a processor operatively coupled to the at least one light detector, wherein the processor receives the first and second signals from the at least one light detector, and wherein, based upon the received first and second signals, the processor repeatedly determines a real-time concentration of hemoglobin within the fluid sample as fluid from the patient is collected in the container, using the processor to determine a current volume of blood within the fluid sample based upon a previously measured hemoglobin concentration of the patient, the determined real-time hemoglobin concentration within the fluid, and the real-time volume of the fluid within the suction canister.

9. The method of claim 8, wherein the light source comprises a plurality of light emitting diodes (LEDs), wherein at least one LED of the plurality of LEDs is configured to emit light at the first wavelength, and wherein at least one LED of the plurality of LEDs is configured to emit light at the second wavelength, and wherein each LED of the plurality of LEDs is configured for selective activation.

10. The method of claim 8, wherein the processor is configured to receive at least one input indicative of the volume of the sample fluid.

11. The method of claim 8, wherein the at least one light detector comprises an array of a plurality of light detectors, and wherein each light detector of the array of light detectors is configured to produce a transmittance signal indicative of the transmittance of light measured by the light detector, and wherein the processor is configured to receive the transmittance signal from each light detector.

12. An apparatus for measuring an amount of blood over time in a fluid sample, comprising:

a surgical suction container for receiving fluid from a patient during a medical or surgical procedure, the fluid including blood of the patient;

at least one light source, the at least one light source generating light at a first wavelength and at a second wavelength different from the first wavelength;

at least one light detector, the at least one light detector positioned in an operative position with respect to the surgical suction container for receiving at least a portion of the light generated by the at least one light source along at least a portion of a vertical axis of the surgical suction container, wherein the at least one light detector receives at least a portion of the light generated by the at least one light source and produces a first signal indicative of a first absorbance of light of the fluid sample at the first wavelength and a second signal indicative of a second absorbance of light of the fluid sample at the second wavelength;

a volume measuring device configured to measure a real-time volume of fluid in the surgical suction container and provide the real-time volume of fluid in the surgical suction container to the processor; and a processor operatively coupled to the at least one light detector, the processor receiving the first and second signals from the at least one light detector, and wherein, based upon the received first and second signals, the real-time volume of fluid in the surgical suction container and a previously measured hemoglobin concentration of the patient, the processor repeatedly determines a real-time concentration of hemoglobin within the fluid sample and a corresponding real-time blood volume within the container based on the real-time concentration of hemoglobin and a real-time volume of the fluid sample within the surgical suction container.

13. The apparatus of claim 12, wherein each light source of the at least one light source comprises a plurality of light emitting diodes (LEDs), wherein at least one LED of the plurality of LEDs is configured to emit light at the first wavelength, and wherein at least one LED of the plurality of LEDs is configured to emit light at the second wavelength, and wherein each LED of the plurality of LEDs is configured for selective activation.

14. The apparatus of claim 12, wherein the at least one light detector comprises an array of a plurality of light detectors, and wherein each light detector of the array of light detectors is configured to produce a transmittance signal indicative of the transmittance of light measured by the light detector, and wherein the processor is configured to receive the transmittance signal from each light detector.

15. The apparatus of claim 12, further comprising an input connected to the processor for input of a previously measured hemoglobin concentration of the blood of the patient into the processor.

16. The apparatus of claim 12, further comprising an input connected to the processor for input of a previously estimated blood loss of the patient.

* * * * *